Figure 1:
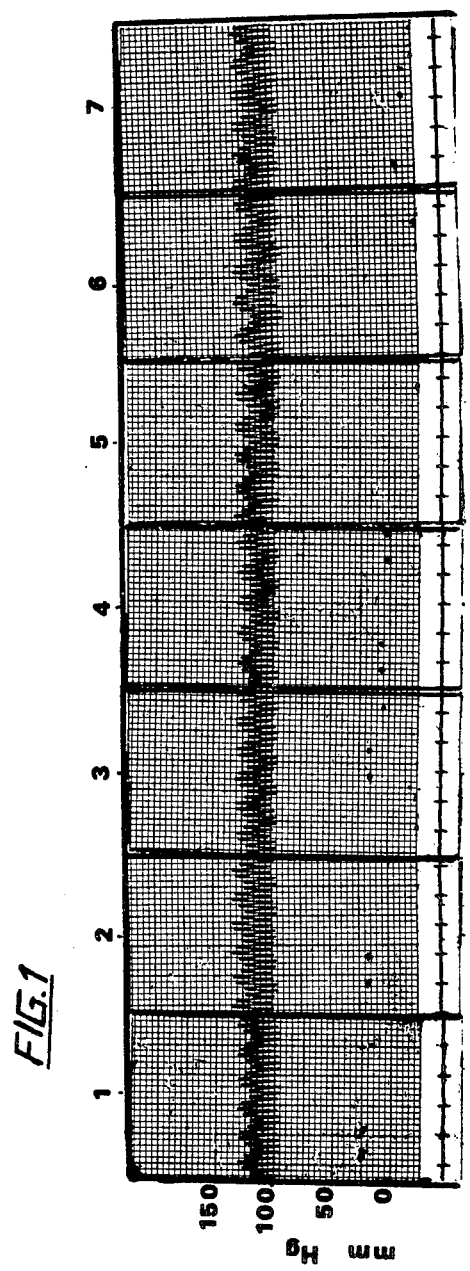

United States Patent [19]

Tosi

[11] 4,191,780
[45] Mar. 4, 1980

[54] BROMHEXINE DERIVATIVES AND PROCESS FOR MAKING SAME

[75] Inventor: Carlo Tosi, Nimis, Italy

[73] Assignee: Instituto Franco Tosi S.p.A., Milan, Italy

[21] Appl. No.: 952,589

[22] Filed: Oct. 16, 1978

[30] Foreign Application Priority Data

May 29, 1978 [IT] Italy ................ 23931 A/78

[51] Int. Cl.$^2$ ............... A61K 31/165; C07C 103/37; C07C 103/19; C07C 103/75
[52] U.S. Cl. ................ 424/324; 260/557 R; 260/558 P; 260/559 B; 260/562 R
[58] Field of Search ........... 260/559 B, 558 P, 562 R, 260/557 R; 424/324

[56] References Cited

U.S. PATENT DOCUMENTS

| | | | |
|---|---|---|---|
| 3,917,696 | 11/1975 | Ferrer et al. | 260/562 R |
| 3,985,804 | 10/1976 | Chiyomaru et al. | 260/558 P |
| 4,123,554 | 10/1978 | Kawada et al. | 260/558 P |

FOREIGN PATENT DOCUMENTS 2337456  4/1975  Fed. Rep. of Germany ....... 260/558 P

*Primary Examiner*—Albert T. Meyers
*Assistant Examiner*—H. Steven Seifert
*Attorney, Agent, or Firm*—Haseltine, Lake & Waters

[57] ABSTRACT

Bromhexine derivatives corresponding to the following general formula

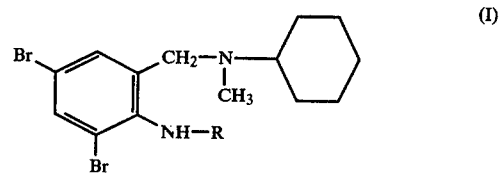

(I)

and antitussive compositions therefrom, as well as a process for making same are described.

3 Claims, 3 Drawing Figures o——o IFT 1026
△------△ Bromexina o———o IFT 1026
△----△ Bromexina

BROMHEXINE DERIVATIVES AND PROCESS FOR MAKING SAME

The present invention concerns novel Bromhexine derivatives possessing lower mucolytic and cough depressing activity with lower toxicity than Bromhexine.

It is known that Bromhexine (N-cyclohexyl-N-methyl-2-(2-amino-3,5-dibromo)benzylammonium chloride) produces a marked stimulation of bronchial secretion and depressing effects on various types of cough in animal experiments (vd. e.g. Englehorn R. and S. Puschmann, 1966, Arzneim-Forsch. 13, 474–480; Merker H. I. Arzneim-Forsch. 16,509,1966; Boyd E. M. and Sheppard P. Arch. Int. Pharmacodyn. 163, 284, 1966).

These effects were confirmed in clinical investigations (e.g. Fischnaller M., SChwarzenberg E. and Wrbk E. Wien, Klin. Wschr. 79,1,1967; Gieseking R., Baldamus U. Beitr. Klin. Tuberk. 137, 1, 1968; Aylward M. Curr. Med. Res. Opin. 1,219,1973; Muittari A., Linnoila M. Curr. Ther. Res. 22,237,1977).

The Bromhexine derivatives of the instant invention may be represented by the following general formula:

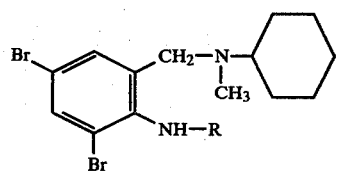
(I)

wherein R = —CO—CH₂—CH₃ (IFT 1021)
= —CO—CH₂—CH₂—CH₃ (IFT 1022)
R = —CO—(CH₂)₅—CH₃ (IFT 1023)

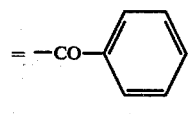 (IFT 1024)

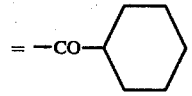 (IFT 1025)

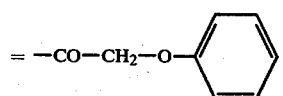 (IFT 1026)

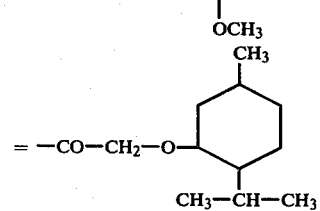 (IFT 1027)

The present invention concerns also a process for making said Bromhexine derivatives which comprises preparing the required carboxylic acid chloride using a chlorinating agent such as, e.g. thionyl chloride, and then reacting an excess of the so-prepared carboxylic acid chloride, in the presence of a suitable solvent such as, e.g. benzene, toluene, methylene chloride, chloroform with Bromhexine. All the inventive Bromhexine derivatives are obtained as hydrochlorides.

The following examples will better illustrate the present invention. The fact that only the preparation of compound IFT 1026 is described extensively should not be construed as restrictive of the scope of patent protection of the instant invention. In fact, the realization of the inventive process may vary in a general manner with respect to the reaction conditions and adapted to the specific circumstances. According to the nature of the starting material the skilled artisan will have no problem in preparing the desired end product.

Preparation of the guaiacol-glycolic acid chloride 220 g (1.20 mol) of guaiacolic acid are gradually added under stirring to 1082 g (9.09 mol–660 ml) of thionyl chloride.

The mixture is then refluxed gently.

After about 3 hours, the exceeding thionyl chloride is evaporated and the oil is distilled off: the fraction which boils at 100°–120° C./1 mm is collected: 213 g of yellow oil (theoretical 242 g) are obtained: yield=87.9%.

Similarily menthyl-glycolic acid chloride is obtained: b.p.=115°–120°/6–7 mm, yield=51%.

Synthesis of IFT 1026

N-(2-guaiacol-glycolyl-amino-3,5-dibromobenzyl)N-cyclohexylmethylamine 213 g of Bromhexine are dissolved under stirring in 1.7 l of anhydrous benzene. Then 129 g (0.64 mol) of guaiacol glycolic acid chloride, dissolved in 1.270 l of dry benzene are added dropwise at room temperature during 0.5 h. The temperature increases to 32° C. The reaction mixture is then heated to reflux for two hours and allowed to stand at room temperature overnight.

The formed precipitate is filtered, washed several times with benzene and dried in vacuo at 60° C. 320 g of white product are obtained: m.p.=190°–192° C. (theoretical 326.6 g; yield=97.9%.

All the synthesized compounds (IFT 1021, IFT 1022, IFT 1023, IFT 1024, IFT 1025, IFT 1026, IFT 1027) are listed in Table No. 1: molecular formulas and weights, melting points of each product (as hydrochloride) and their yields are reported.

PHARMACOLOGY

(1) Acute toxicity

In rats treated with increasing doses up to 3000 mg/kg of IFT 1026 orally, no lethal cases are observed up to the seventh day after treatment.

Only a slight depression in behaviour, occasional tremor and stiffness with the high doses are recorded.

The results of toxicity tests on mice treated i.p. are shown in Table No. 2.

(2) Long-term Toxicity in Rats

Long-term toxicity (16 weeks) of IFT 1026 is tested in comparison to the parent compound (Bromhexine). The mean body weight data are given in Table No. 3. As it may be seen, there are no significant variations in the body weights, except that the groups receiving 1000 mg/kg/day of Bromhexine show lower values than their control group.

Urine analysis is carried out on 6 animals per group (3 males and 3 females) before as well as 30 and 60 days after treatment. Control group and the animals receiving 250 mg/kg Bromhexine and 350 mg/kg IFT 1026 respectively are observed.

The amount, aspect, colour, pH value, albumin, glucose, bilirubin levels and ketone bodies are recorded using also Ames reactive stripes.

The data show that no changes occur in said parameters, thus evidencing that the treatment with IFT 1026 causes no impairment in the kidney.

The hematological and biochemical values relating to the groups under treament with the above reported doses are shown in Tables Nos. 4 and 5. These values are virtually the same for both treated and control animals.

The possibility to use BSP for the diagnosis of lesions in liver parenchyma is well known. Bromsulphtalein (BSP) clearance was made according to Carpi and Parenti (Carpi, C. and M. A. Parenti, Il Farmaco, Ed. Pr. vol. 17, page 45, 1962). Thirty minutes after the i.v. administration of 50 mg/kg BSP to control rats, the mean plasma level of the dyestuff is 80±12 mcg/ml. The data obtained for the rats treated with the lower does of drug are shown in Table No. 6.

Organ weights obtained at necropsy are reported in Table No. 7. No gross pathological changes are observed with respect to controls. Four rats treated with the highest dose of Bromhexine display liver steatosis. Five animals treated with 1000 mg/kg Bromhexine and 2 animals treated with 70 mg/kg of IFT 1026 died during this study. Therefore, on the basis of these findings, it may be concluded that IFT 1026 is less toxic than Bromhexine for rats at the administered doses.

(3) Action on blood pressure and heart rate

After intraperitoneal administration of increasing doses of IFT 1026, blood pressure, heart rate and the amplitude of heart contractions are unchanged. The effect of IFT 1026 at the dose of 450 mg/kg on blood pressure in the anesthesized rat is exemplified by the graph in FIG. No. 1.

(4) Action on the amphetamine-induced stereotypies and Toxicity on mice. Action on the CNS Stereotypies and death are caused 60 min. after treatment with IFT 1026 (500 mg/kg/10 ml p.o.) by injecting dl-amphetamine (16 mg/kg/ml i.p.) to groups of 10 male albino Swiss mice per cage. Stereotypies and death are not changed by previous oral administration of IFT 1026.

(5) Study of analgesic action on mice

Two test methods are used for establishing the action of Bromhexine and IFT 1026 on noci-ceptive stimuli in mice.

(a) Pain induced by a chemical stimulus according to the method of Siegmund (Siegmund E., Cadmier, R., and Lu, G. Proc. Soc. exp. Biol. N.Y. 95, 729—1957). The mice distributed at random into groups of 10 animals, are deprived of solid food for the 18-hour period prior to the test. The compounds are administered orally at the dose of 300 mg/kg; controls are treated by the same routes with equivalent amounts of inactive excipients (10 ml/kg). Thirty minutes after treatment the mice are injected i.p. with 0.1 ml/10 g of a 1.5% acetic acid solution. The writhing is recorded for a 20 min. period following this i.p. injection.

(b) Pain induced by a physical stimulation according to the hot-plate test technique by Eddy and Leimbach (Eddy, N. B. and Leimbach, O., J. Pharmacol. exp.Ther. 107, 383—1953). The temperature of the plate was kept at 57° C. Groups of 12 mice are treated as described under (a) above. The reaction times are measured 15 min. before treatment ($R_o$) and 4 times after the administration (every 15 min). Only the maximal response is taken into account ($R_{max}$). Responses to algogenic stimuli are not suppressed after administration of IFT 1026 and Bromhexine. The results are shown in Table No. 8.

(6) Antitussive effect in Guinea-pigs and mice

Cough is elicited by 15% citric acid spray in both species, according to the method by Harsany et al. (Boll. Chim. Farm. 112, 691, 1973). The effect was tested 1 hour after oral administration and 30 min. after intraperitoneal application of the antitussive agents on mice and Guinea-pigs respectively.

$ED_{50}$ values of the drugs are computed by the method of Litchfield and Wilcoxon (Litchfield, J. T. Jr., and Wilcoxon F., J. Pharmacol. exp. Ther. 96,99—1949).

FIG. Nos. 2 and 3 show the individual dose-response curves of comparative experiments with IFT 1026 and Bromhexine. The calculated $ED_{50}$'s are shown in Table No. 9. The antitussive effect of IFT 1026 is slightly weaker than Bromhexine; however, it is the same when compared in terms of the parent compound.

CONCLUSIONS

Acute toxicity of the compound in terms of $LD_{50}$ has not been estimated due to the very low toxicity of the drug.

Rats receiving IFT 1026 every day for 16 consecutive weeks show no significant changes not only in the general state of health with respect to behaviour and body weight, but also with respect to blood and viscera. This denotes that the long-term toxicity in the rats is also weak. Furthermore, subacute and long-term administration also evidences that the inventive compound is less toxic than the parent compound.

The antitussive effect in mice and Guinea-pigs is approximately the same as that of Bromhexine. This denotes a better therapeutic index for IFT 1026.

This drug showed neither analgesic nor undesired side-effects on blood pressure and heart rate.

The absence of any analgesic effect shows that this compound has no specific psychotropic properties. Moreover, this drug has no hypotensive action, differing from the opiates, in particular codeine.

TABLE No. 1

| Compounds | Formula | M.W. | m.p., °C. | Yield % |
|---|---|---|---|---|
| IFT 1021 | $C_{17}H_{24}Br_2N_2O \cdot HCl$ | 468,64 | 224°–227°(dec.) | 80% |
| 1022 | $C_{18}H_{26}Br_2N_2O \cdot HCl$ | 482,66 | 187°–189° | 74% |
| 1023 | $C_{21}H_{32}Br_2N_2O \cdot HCl$ | 524,74 | 199°–201° | 71% |
| 1024 | $C_{21}H_{24}Br_2N_2O \cdot HCl$ | 516,68 | 253°–255°(dec.) | 78% |
| 1025 | $C_{21}H_{30}Br_2N_2O \cdot HCl$ | 522,74 | 244°–247°(dec.) | 59% |
| 1026 | $C_{23}H_{28}Br_2N_2O_3 \cdot HCl$ | 576,73 | 190°–192° | 90% |
| 1027 | $C_{26}H_{40}Br_2N_2O_2 \cdot HCl$ | 608.86 | 199°–200° | 51% |

TABLE No. 2

Eight-day toxicity studies of IFT 1026 and Bromhexine in mice. Lethality.

| Treatment | Daily dose mg/k | Number of deaths at day | | | | | | | | Total number of deaths |
|---|---|---|---|---|---|---|---|---|---|---|
|  |  | 1 | 2 | 3 | 4 | 5 | 6 | 7 | 8 |  |
| IFT 1026 | 450 |  |  | 1 |  |  |  |  |  | 1/10 |
| IFT 1026 | 900 |  | 1 |  |  |  |  |  |  | 1/10 |
| Bromhexine | 300 |  |  | 1 |  |  | 1 |  |  | 2/10 |

TABLE No. 2-continued

Eight-day toxicity studies of IFT 1026 and Bromhexine in mice. Lethality.

| Treatment | Daily dose mg/k | Number of deaths at day 1 | 2 | 3 | 4 | 5 | 6 | 7 | 8 | Total number of deaths |
|---|---|---|---|---|---|---|---|---|---|---|
| Bromhexine | 600 | | | 1 | | 1 | 1 | 1 | 1 | 5/10 |

TABLE No. 3

Effect of daily oral administration of various doses of IFT 1026 and Bromhexine on mean body weight of rats. (n = 7/each group).

| Treatment | mg/kg | Changes in body weight (g) Mean ± SE (Females) 0 days | 21 days | 45 days | 60 days |
|---|---|---|---|---|---|
| Controls | | 114 ± 4 | 170 ± 5 | 214 ± 7 | 225 ± 14 |
| Bromhexine | 50 mg | 110 ± 5 | 174 ± 2 | 217 ± 4 | 229 ± 4 |
| Bromhexine | 250 mg | 109 ± 6 | 158 ± 5 | 206 ± 4 | 230 ± 3 |
| Bromhexine | 1000 mg | 117 ± 6 | 147 ± 13 | 157 ± 7 | 188 ± 12 |
| IFT 1026 | 70 mg | 125 ± 6 | 181 ± 5 | 218 ± 2 | 242 ± 2 |
| IFT 1026 | 350 mg | 118 ± 2 | 179 ± 5 | 225 ± 7 | 232 ± 10 |
| IFT 1026 | 1400 mg | 122 ± 5 | 173 ± 7 | 211 ± 5 | 221 ± 8 |

TABLE No. 3-continued

Effect of daily oral administration of various doses of IFT 1026 and Bromhexine on mean body weight of rats. (n = 7/each group).

| Treatment mg/kg | | Mean ± SE (Males) 0 days | 21 days | 45 days | 60 days |
|---|---|---|---|---|---|
| Controls | | 120 ± 5 | 223 ± 8 | 300 ± 6 | 368 ± 5 |
| Bromhexine | 50 mg | 115 ± 9 | 225 ± 6 | 295 ± 7 | 365 ± 7 |
| Bromhexine | 250 mg | 118 ± 12 | 218 ± 7 | 285 ± 8 | 355 ± 9 |
| Bromhexine | 1000 mg | 110 ± 7 | 180 ± 9 | 250 ± 8 | 290 ± 12 |
| IFT 1026 | 70 mg | 117 ± 7 | 220 ± 4 | 310 ± 4 | 370 ± 6 |
| IFT 1026 | 350 mg | 123 ± 8 | 226 ± 6 | 290 ± 7 | 368 ± 4 |
| IFT 1026 | 1400 mg | 121 ± 5 | 222 ± 7 | 295 ± 8 | 365 ± 9 |

S.E. = Statistical Error

TABLE No. 4

Effect of daily oral administration of Bromhexine 250 mg/kg and IFT 1026 350 mg/kg on the hematological parameters in the rat. Mean ± SE.

| Treatment | Males | | | Females | | |
|---|---|---|---|---|---|---|
| | RBC $10^6$/ml | WBC $10^2$/ml | Hb g/100 ml | RBC $10^6$/ml | WBC $10^2$/ml | Hb g/100 ml |
| Controls | 763 ± 50 | 153 ± 26 | 14.1 ± 1,0 | 740 ± 30 | 154 ± 14 | 12.9 ± 15 |
| Bromhexine | 774 ± 63 | 168 ± 20 | 15.3 ± 1,6 | 752 ± 37 | 132 ± 5 | 14.8 ± 1,4 |
| IFT 1026 | 657 ± 60 | 140 ± 10 | 13.3 ± 1,4 | 817 ± 58 | 179 ± 26 | 12.8 ± 1,1 |

TABLE No. 5

Effect of daily oral administration of 250 mg/kg Bromhexine and 350 mg/kg IFT 1026 on biochemical parameters in the rat. Mean ± SE.

| Treatment | | SGPT Units/ml | SGOT Units/ml | BUN mg % | GLUCOSE mg % | TOTAL PROTEIN mg/ml | A/G ratio |
|---|---|---|---|---|---|---|---|
| Controls | males | 13.4 ± 0.5 | 25.9 ± 0.5 | 44.8 ± 7 | 76.2 ± 8 | 30.5 ± 3.5 | 2.2 ± 0.2 |
| | females | 13.1 ± 0.6 | 23.4 ± 0.4 | 42.9 ± 3 | 93.3 ± 9 | 31.3 ± 2.4 | 2.5 ± 0.3 |
| Bromhexine | males | 12.7 ± 0.15 | 24.8 ± 0.5 | 34.5 ± 3 | 88.5 ± 6 | 27.1 ± 2.5 | 2.4 ± 0.2 |
| | females | 12.6 ± 0.3 | 24.1 ± 0.5 | 44.9 ± 4 | 77.1 ± 9 | 25.8 ± 1.1 | 2.6 ± 0.1 |
| IFT 1026 | males | 13.1 ± 0.7 | 24.5 ± 0.6 | 39.9 ± 5 | 73.7 ± 5 | 28.2 ± 2.1 | 2.2 ± 0.1 |
| | females | 13.2 ± 0.4 | 25.1 ± 0.3 | 41.1 ± 2 | 85.9 ± 8 | 30.6 ± 2.4 | 2.6 ± 0.3 |

SGPT = serum glutamic pyruvic transaminase
SOGT = serum glutamic oxalatetic transaminase
BUN = blood urea nitrogen
A/G ratio = Albumin/Globulin ratio TABLE No. 6

% of rate showing BSP plasma levels greater than 80 mcg/ml (control values) and 160 mcg/ml (two-fold control values)

| Treatment | >80 mcg/ml number/tested | % | >160 mcg/ml number/tested | % |
|---|---|---|---|---|
| Bromhexine | 7/17 | 41 | 2/17 | 12 |
| IFT 1026 | 5/18 | 28 | 1/18 | 5.5 |
| | $X^2 = 0.7$ | N.S. | $X^2 = 0.43$ | N.S. |

TABLE No. 7

Effect of daily oral administration of 250 mg/kg Bromhexine and 350 mg/kg IFT 1026 on organ weights of rats, expressed as grams of fresh weight.

| Treatment | | Liver | Brain $10^{-1}$ | Lungs $10^{-1}$ | Heart $10^{-1}$ | Spleen $10^{-1}$ | Kidneys $10^{-1}$ | Adrenal glands $10^{-2}$ |
|---|---|---|---|---|---|---|---|---|
| Controls | males | 11.2 ± 0.2 | 16.6 ± 0.5 | 11.6 ± 0.4 | 7.6 ± 0.3 | 6.6 ± 0.3 | 18 ± 0.5 | 4.1 ± 0.11 |
| | females | 10.3 ± 0.1 | 18.8 ± 0.7 | 15.2 ± 0.8 | 8.1 ± 0.4 | 7 ± 0.6 | 18.9 ± 1 | 4.8 ± 0.1 |
| Bromhexine | males | 10.6 ± 0.2 | 14 ± 1 | 11.6 ± 1.7 | 8.8 ± 1.4 | 6 ± 0.6 | 18.4 ± 0.5 | 3.8 ± 0.2 |
| | females | 10.5 ± 0.2 | 19.7 ± 0.5 | 14.4 ± 0.9 | 8.3 ± 0.2 | 7.9 ± 0.2 | 18.8 ± 0.9 | 4.7 ± 0.1 |
| IFT 1026 | males | 9.7 ± 0.9 | 13.4 ± 0.4 | 9.1 ± 0.8 | 7.1 ± 0.4 | 6.3 ± 0.3 | 18.3 ± 0.4 | 3.7 ± 0.5 |
| | females | 10.1 ± 0.3 | 19.4 ± 1 | 14.2 ± 1.1 | 7.3 ± 0.8 | 6.5 ± 0.2 | 18.2 ± 0.4 | 4.6 ± 0.1 |

TABLE No. 8

Analgesic action in the mouse. For heat stimulus the reaction time in sec. was recorded. For chemical stimulus the number of writhings for a 20 min. period was observed. Mean ± SE.

| Treatment mg/kg | Siegmund Test | Hot-plate Test (R max/$R_o$) |
|---|---|---|
| Controls | 34 ± 1 | 1.3 ± 0.09 |
| Bromhexine 300 | 32 ± 3 | 1.5 ± 0.18 |
| IFT 1026 300 | 34 ± 3 | 1.62 ± 0.26 |

TABLE No. 9

| | Antitussive activity in mice and Guinea-pigs. | | | |
|---|---|---|---|---|
| | MICE | | GUINEA-PIGS | |
| Treatment | $ED_{50}$ mg/kg | CONFIDENCE LIMITS (P = 0.05) | $ED_{50}$ mg/kg | CONFIDENCE LIMITS (P = 0.05) |
| IFT 1026 | 298 | 249 ÷ 346 | 189 | 132 ÷ 246 |
| BROMHEXINE | 194 | 155 ÷ 233 | 143 | 102 ÷ 184 |

Figure 2:
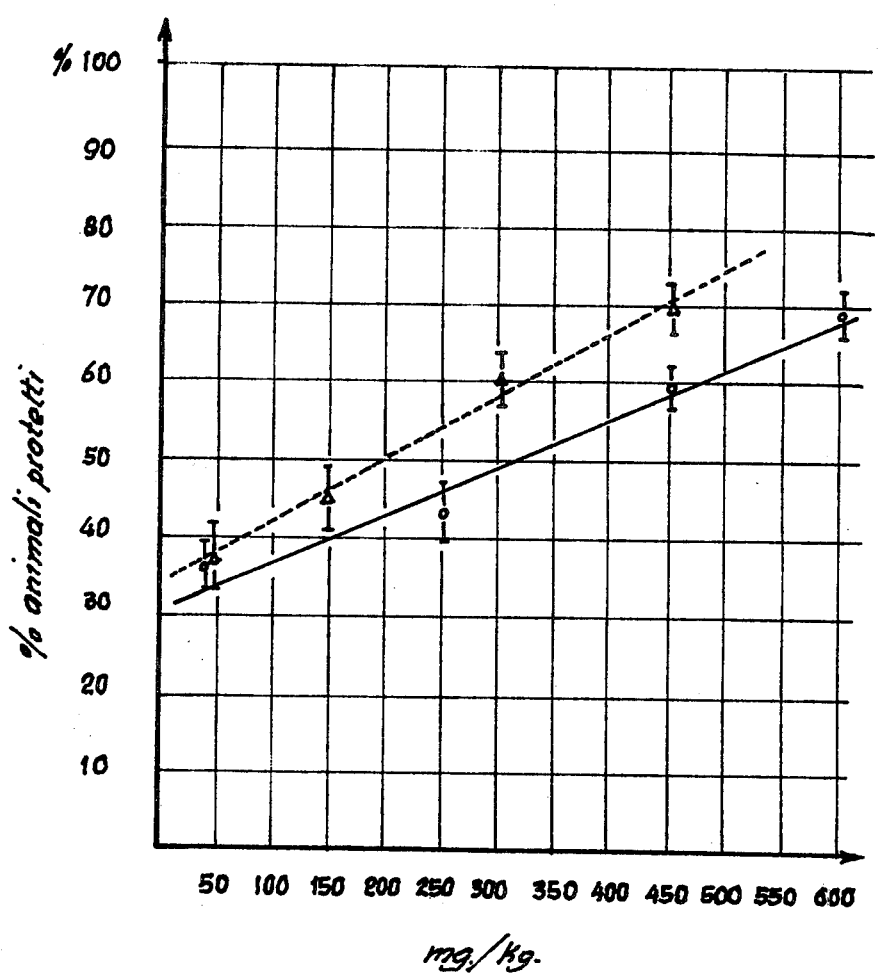
Figure 3:
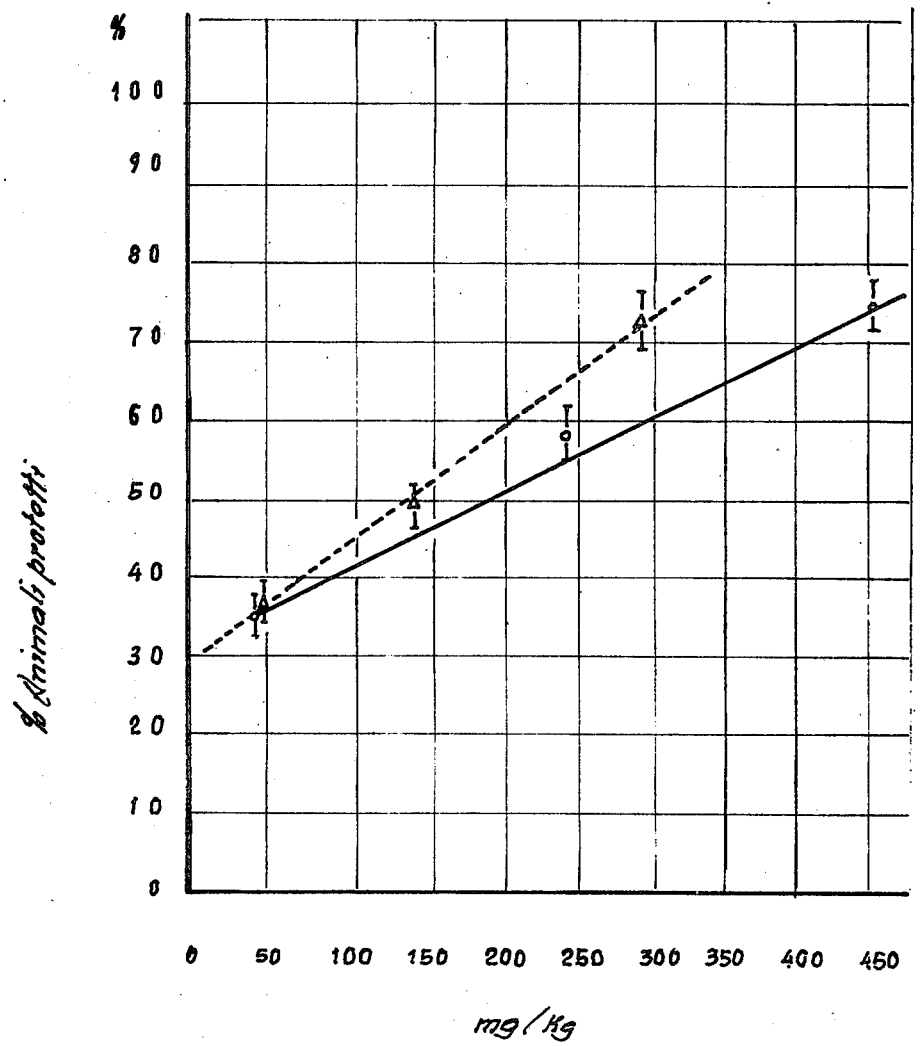

FIGS. 1 through 3 are described as follows:

FIG. 1—Arterial pressure recorded in the anaesthetized rat before and after IFT 1026 administration.
1 = base value
2 = 5 min. after treatment
3 = 10 min. after treatment
4 = 15 min. after treatment
5 = 30 min. after treatment
6 = 45 min. after treatment
7 = 60 min. after treatment FIG. 2—Antitussive activity of IFT 1026 and Bromhexine. Oral administration to the mouse.
o—o: IFT 1026
△- - - -△: Bromhexine FIG. 3—Antitussive activity of IFT 1026 and Bromhexine. Intraperitoneal administration to the Guinea-pig.
o—o: IFT 1026
△- - - -△: Bromhexine

I claim:

1. A compound selected from the group consisting of those of the formula

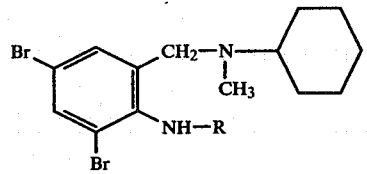

wherein R is

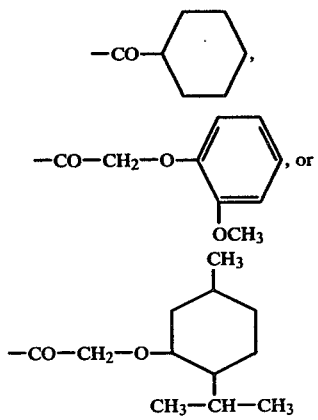

and the acid addition salts thereof.

2. A compound of Formula I as defined in claim 1 which is N-(2-quaicol-glycolyl-amino-3,5-dibromobenzyl)N-cyclohexylmethylamine or the hydrochloride salt thereof.

3. Pharmaceutical composition comprising an antitussive effective amount of a compound of formula I in claim 1 or its acid addition salt in a pharmaceutically acceptable carrier.

* * * * *